United States Patent [19]
Münzenberg et al.

[11] Patent Number: 5,847,145

[45] Date of Patent: Dec. 8, 1998

[54] ALKYLALKOXYSILYL-1,3-OXAZOLINES, A METHOD OF PRODUCTION AND USE

[75] Inventors: Jörg Münzenberg, Hanau; Rolf Mülhaupt, Freiburg; Philipp Müller, Gundelfingen, all of Germany

[73] Assignee: Degussa Aktiengesellschaft, Frankfurt am Main, Germany

[21] Appl. No.: 803,372

[22] Filed: Feb. 20, 1997

[30]   Foreign Application Priority Data

Feb. 21, 1996 [DE] Germany ................. 196 06 413.9

[51] Int. Cl.⁶ ............................................. C07F 7/18
[52] U.S. Cl. ........................................................ 548/110
[58] Field of Search .................................. 548/237, 110

[56]   References Cited

PUBLICATIONS

Organosilicon 1,3 Oxazolines: Reactive Silicone Liquid Rubbers and Silane Agents etc. Mueller et al. Polymer Mater. Sci. Eng. (1997) vol. 76, pp. 51–52.

Mueller, Philipp et al., "Organosilicon 1,3–oxazolines: reactive silicone liquid rubbers and silane coupling agents tailored for reactive processing application and nanocomposite formation," Chemical Abstracts, vol. 126, No. 22, Jun. 2, 1997, Columbus, OH, abstract No. 294446, XP002053180.

Schaefer, R., et al., "FTIR spectroscopic studies on the interfacial reactions of oxazoline–functionalized polymers," Chemical Abstracts, vol. 125, No. 4, Jul. 22, 1996, Columbus, OH, abstract No. 34317, XP002053181.

Cai, Gangfeng, et al., "Poly(N–acylethylenimine) copolymers containing pendant pentamethyldisiloxanyl groups. II. Thermal behavior and x–ray diffraction study," J. Polym. Sci., Part A: Polym. Chem., (1992), 30(4), 659–69 Coden: JPACEC; ISSN: 0887–624X, XP002053177.

Cai, Gangfeng, et al., "Poly(N–acylethylenimine) copolymers containing pendant pentamethyldisiloxanyl groups. III. Surface prperties and adhesion," J. Polym Sci., Part A: Polym. Chem. (1992), 30(4), 671–7 Coden: JPACEC; ISSN: 0887–624X; XP002053178.

Cai, Gangfeng, et al., "Poly(N–acylethylenimine) copolymers containing pendant pentamethyldisiloxanyl groups. I. Synthesis," J. Polym. Sci., Part A: Polym. Chem. (1992), 30(4), 649–57 Coden: JPACEC; ISSN; 0887–624X; XP002053179.

*Primary Examiner*—Johann Richter
*Assistant Examiner*—Ebenezer Sackey
*Attorney, Agent, or Firm*—Beveridge, DeGrandi, Weilacher & Young, LLP

[57]   ABSTRACT

Alkylalkoxysilyl-1,3-oxazolines, their production by reacting 2[-alkenyl]-1,3-oxazolines with alkylalkoxysilanes or cyano alkylene silane compounds with amino alcohols and the use of the compounds for modifying materials with siliceous surfaces.

18 Claims, 2 Drawing Sheets

ALKYLALKOXYSILYL-1,3-OXAZOLINES, A METHOD OF PRODUCTION AND USE

FIELD OF THE INVENTION

This invention relates to alkylalkoxysilyl-1,3-oxazolines and methods of producing the same. More particularly, it relates to a siliceous materials having a surface that is modified with these oxazoline compounds and methods for producing the modified siliceous materials, as well as plastics containing the modified siliceous materials and a process for producing them.

BACKGROUND OF THE INVENTION

In the past, fillers have been added to plastics to improve the properties of plastics. According to U.S. Pat. No. 4,868,226, fillers for improving polyethylene resins included organic or inorganic fillers, for example, silica. The filler according to that invention could also be subject to surface treatment in order to keep a balance between rigidity and impact strength of the polyethylene. For example, organosilane compounds were used as surface treating agents for fillers which were then added to polypropylene resins.

SUMMARY OF THE INVENTION

One object of the invention is to improve the properties of plastics, such as tensile strength. Material having siliceous surfaces can be modified with novel compounds according to the invention which then can be added to plastics such as polypropylene.

Thus, an object of the invention is to provide compounds and modified materials having siliceous surfaces modified by these compounds. A further object of the invention is to provide the method for making the compounds and for modifying materials having siliceous surfaces with the compounds. Another object is to provide plastic resins having improved properties, and which contain the modified siliceous materials and a method for producing the same.

Accordingly, the compounds and methods in accordance with the invention are compounds which are alkylalkoxysilyl-1,3-oxazolines of the general formula

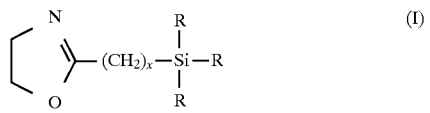
(I)

wherein R is a member selected from the group consisting of alkyl with 1 to 6 C atoms, branched or unbranched, alkoxy with 1 to 4 C atoms, and phenyl wherein Si is bonded to at least one alkoxy group; and wherein x signifies a whole number from 2 to 14.

A method of producing the alkylalkoxysilyl-1,3-oxazolines as defined above comprises reacting 2-(alkenyl)-1,3-oxazoline of the general formula

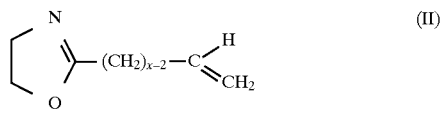
(II)

wherein x is a whole number of 2 to 14 with an alkylalkoxysilane of the general formula

(III)

wherein R is a member selected from the group consisting of branched or unbranched alkyl having 1–6 carbon atoms, alkoxy having 1–4 carbon atoms, or phenyl, wherein the 2-(alkenyl)-1,3-oxazoline and alkylalkoxy silane is reacted in the presence of a Pt or rhodium catalyst.

A method of producing the alkylalkoxysilyl-1,3-oxazolines as defined above can also be achieved by reacting an amino alcohol with a cyanosilane compound of the general formula

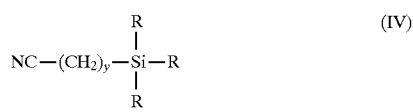
(IV)

wherein R is a member selected from the group consisting of branched or unbranched alkyl having 1–6 carbon atoms, alkoxy having 1–4 carbon atoms, or phenyl, and y is a whole number from 2 to 12. The 2-(alkenyl)-1,3-oxazoline and alkylalkoxy silane is reacted in the presence of a Pt or rhodium catalyst. The amino alcohol and the cyanosilane compound is reacted in the presence of a Cd salt acting as catalyst.

A modified siliceous material comprises alkylalkoxysilyl-1,3-oxazolines and a material having a siliceous surface. The alkylalkoxysilyl-1,3-oxazolines is bonded to the siliceous surface of the material to form a modified siliceous material.

A method for producing modified siliceous material comprises reacting the alkylalkoxysilyl-1,3-oxazolines with hydroxyl groups on the siliceous surface of a material to form a modified material with the general formula

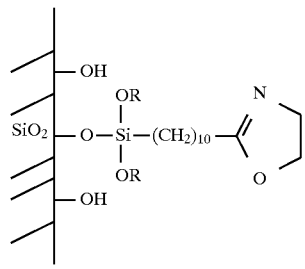

Plastics according to the invention can be made by adding the modified siliceous material which comprises the alkylalkoxysilyl-1,3-oxazolines to the plastics.

DETAILED DESCRIPTION OF THE INVENTION

Figure 1:
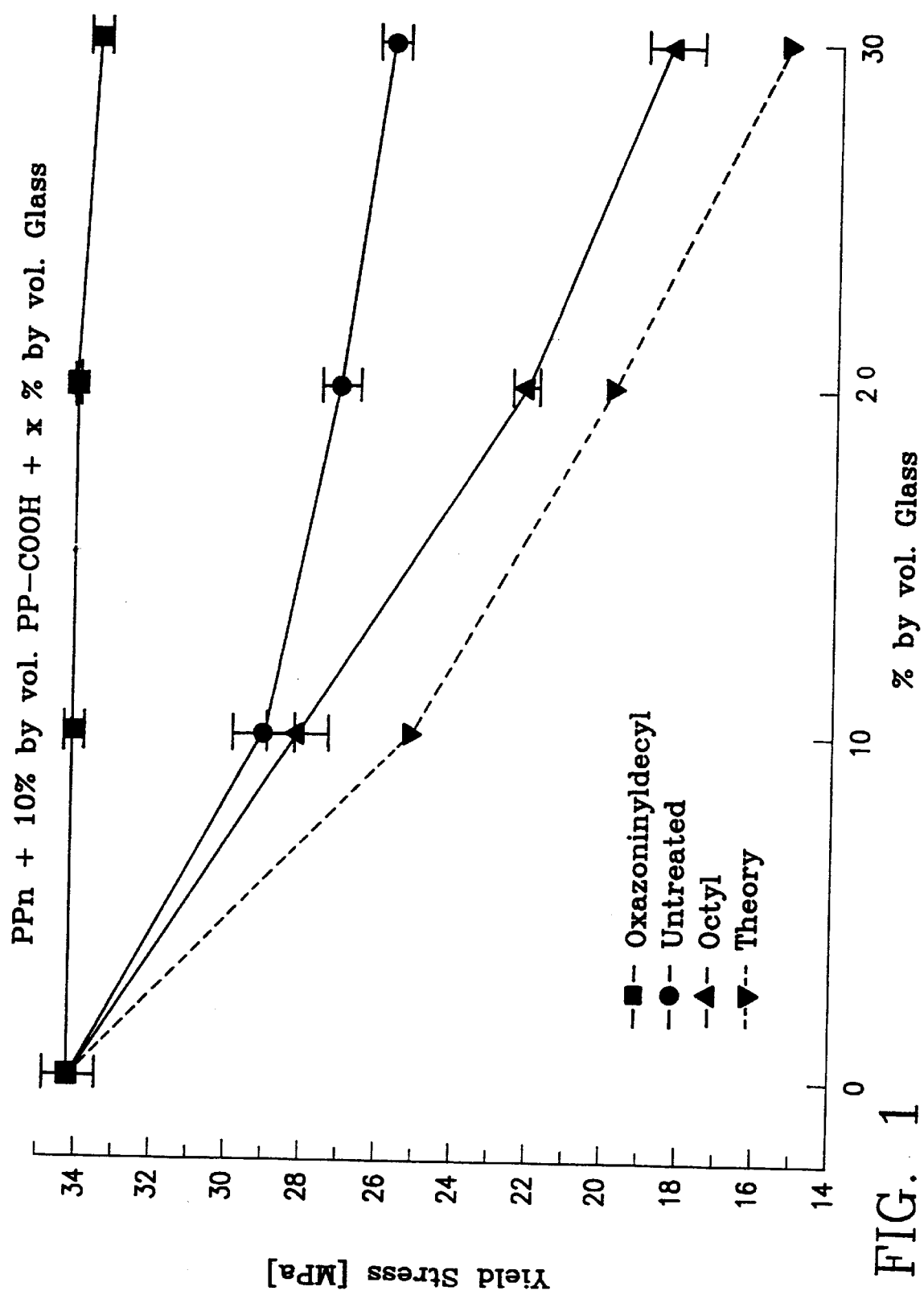
FIG. 1: The results of the Series I experiments as listed in Table 1 are graphed comparing the tensile stress of polypropylene, which contains oxazoline-functionalized glass spheres covalently bonded to carboxylated polypropylene according to the invention, with polypropylene that contains untreated glass spheres or glass spheres that do not contain the oxazoline compound according to the claimed invention. The volume of the adhesion promoter (carboxylated polypropylene) in the Series I experiments was held constant at 10% by volume. The volume of the glass sphere filler was varied, and the results were graphed at 0%, 10%, 20%, and 30% by volume.

The compounds in accordance with the invention have the general formula

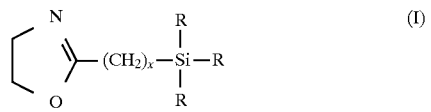

in which

R signifies alkyl with 1 to 6 C atoms, branched or unbranched, alkoxy with 1 to 4 C atoms, phenyl and Si is substituted by at least one alkoxy group, and x signifies a whole number of 2 to 14.

The invention also has as subject matter a method of producing the alkoxysilyl oxazolines according to claim 1, characterized in that a 2-(alkenyl)-1,3-oxazoline of the general formula

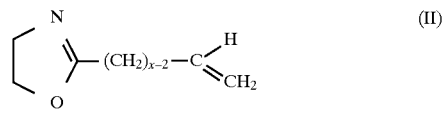

in which x has the meaning given above is reacted in the presence of a Pt or rhodium catalyst with an alkylalkoxysilane of the general formula

in which R has the same meanings as above.

It is preferable to use triethoxy- or trimethoxysilane.

The reaction takes place at temperatures from 80° to 140° C., optionally under the pressure adjusted by the vapor pressure of the reactants and solvents at these temperatures and optionally under protective gas.

In general, the particular initial oxazoline compound is used as solvent. However, it is just as possible to work using inert, organic solvents which dissolve the reactants.

The alkenyl-1,3-oxazoline and the silane to be used are used in a molar ratio of 1:1 to 2.0:1, especially 1.2:1 to 1.7:1.

The hydrosilylation catalysts are known from the state of the art. Hexachloroplatinic acid or coordination complexes such as e.g. RhCl(PPh$_3$)$_3$, optionally in the presence of peroxidic compounds, are suitable.

In a further variation of the method, the compounds in accordance with the invention are produced by a method which is characterized in that a cyanosilane compound of the general formula

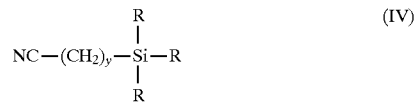

in which R has the meaning given above and y is a whole number from 2 to 12 is reacted with 2-aminoethanol in the presence of a Cd salt acting as catalyst, optionally under protective gas.

The reaction generally takes place at a temperature of from 60° to 140° C., optionally under the pressure being produced at these temperatures by the vapor pressure of the components of the reaction mixture. The cyanosilane compound and the 2-aminoethanol are generally used in a molar ratio of 1.2:1 to 1:1.2. Soluble cadmium salts in a molar amount of 0.1 to 3% relative to the amount of cyanosilane compound are used as catalyst. An inert, organic compound, especially alcohols with 1 to 4 C atoms, branched or unbranched, are selected as solvent. The danger of re-esterification to a homogeneity as regards the substituents in formula IV must naturally be watched for.

The compounds of the invention are used in the modification of siliceous surfaces. This includes, e.g. surfaces of glass fibers, glass spheres, balls, or pellets and also precipitated silicas with a specific surface of 5 to 800 m$^2$/g or pyrogenically obtained silicas with correspondingly high surfaces like those known for the reinforcement of plastics. Methods for the modification of siliceous surfaces can be obtained from the state of the art. It is customary e.g. in the case of glass fibers to immerse these materials in the corresponding, appropriate solutions of the organosilane compounds and to spray with a solution or the pure product.

In the case of fine fillers a spraying of the powder with simultaneous intensive mixing has also proven itself.

The concentrations of the silyl-1,3-oxazolines used fluctuate between 0.01 and 15 parts by weight relative to the material to be modified.

The reaction with the OH groups located on the surface of these materials take place e.g. according to the following scheme:

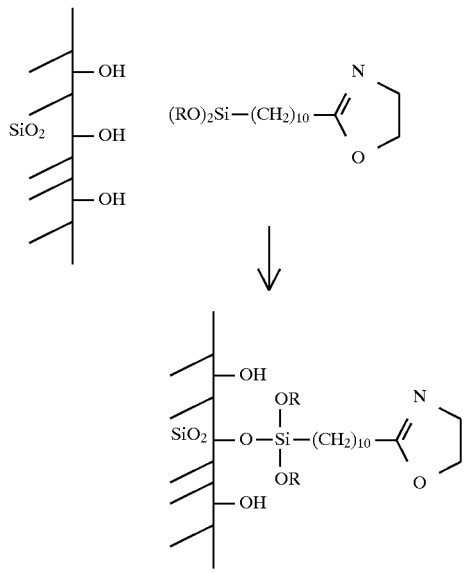

This reaction preferably takes place under alkaline catalysis, that is, in the presence of e.g. ammonium compounds soluble in the system or of further amines.

The glass fibers, glass spheres, silicas, etc. modified in accordance with the invention are used in plastics preferably containing double bonds such as e.g. polypropylene. Carboxylated types in which e.g. the following coupling mechanism is observed are particularly suitable:

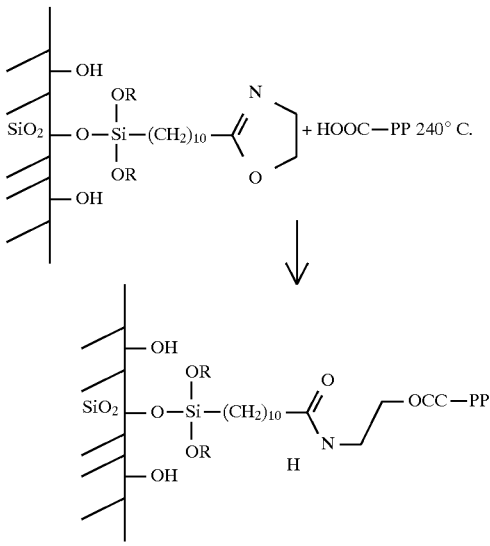

If glass spheres modified with the compounds of the invention are used e.g. in carboxylated propylene the maximum tensile stress of the non-filled matrix theoretically possible is achieved. In contrast thereto, materials treated with octyl silane exhibit a significantly reduced tensile stress.

EXAMPLES

1. Synthesis of alkylalkoxysilyl oxazolines

Production of 2-[10-triethoxysilyl)decyl]-1,3-oxazoline and 2-[10-(trimethoxysilyl)decyl]-1,3-oxazoline

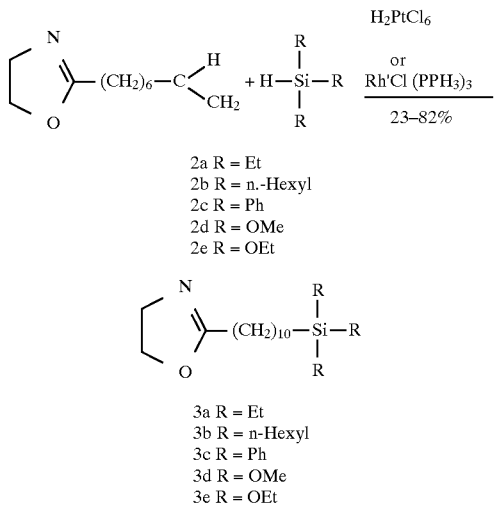

1.1 Example 1

Production of 2-[10-(triethoxysilyl)decyl]-1,3-oxazoline

A mixture of
  34.3 g (0.163 mole) 2-(9-decenyl)-1,3-oxazoline,
  17.9 g (0.109 mole) triethoxysilane,
  0.2 g (0.22 mmole) Rh[1]Cl (PPh$_3$)$_3$, and
  0.29 ml (0.87 mmole) t-butylhydroperoxide (3M solution in toluene)

was heated for 1 h to 100° C. in a round-bottomed flask with internal thermometer and inlet tube for protective gas. The fractionated vacuum distillation of the batch yielded 33.5 g (82% of theory) 2-[10-(triethoxysilyl)decyl]-1,3-oxazoline at a boiling point of 148°–150° C. (0.1 mbar).

FTIR (KBr): ν=2920, 1669 (C=N), 1105, 950 (oxazoline) cm$^{-1}$. $^1$H NMR (300 Mhz, CDCl$_3$): δ=0.63 (2H, t,J=7.9 Hz), 1.21 (23H,m) 1.64 (2H,m), 2.22 (2H,t,J=7.0 Hz), 380 (8H,m), 4.17 (2H,t,J=9.4 Hz). $^{13}$C NMR (75 Mhz, CDCl$_3$): δ=10.2, 18.1, 22.6, 25.8, 27.8, 29.1, 29.1, 29.2, 29.2, 29.3, 33.0, 54.2, 58.1, 66.9, 168.5 C$_{19}$H$_{39}$NO$_4$Si calc. C 61.08 H 10.52 N 3.75 (373.57) obs. 60.88 10.58 3.80 MS (EL): m/z=373 (M$^+$, 10), 85 (100), 98 (72) HRMS: m/z calc. For C$_{19}$H$_{39}$NO$_4$Si 373.2648, obs. 373.2654

1.2 Example 2

Production of 2-[10-(trimethoxysilyl)decyl]-1,3-oxazoline

A mixture of
  3.95 g (18.9 mmoles) 2-(9-decenyl)-1,3-oxazoline,
  1.92 g (15.7 mmoles) trimethoxysilane,
  0.18 ml ((0.008 mmoles) H$_2$PtCl$_6$.aq (0.044M in diglyme)

was heated in a round-bottomed flask with internal thermometer and inlet tube for protective gas for 15 h to 100° C. The fractionated vacuum distillation of the batch yielded 2.1 g (41% of theory) 2-[10-(trimethoxysilyl)decyl]-1,3-oxazoline at a boiling point of 133–135° C. (0.1 mbar).

IR(KBr): ν=2920, 1668, 1110, 950 cm$^{-1}$ $^1$H NMR (300 Mhz, CDCl$_3$): δ=0.61 (2H,t,J=7.9 Hz), 1.23 (14H,m), 1.68 (2H,m), 2.23 (2H,t,J=7.0 Hz), 3.48 (9H,s), 3.78 (2H,t,J=9.4 Hz), 4.17 (2H,t,J=9.4 Hz) $^{13}$C NMR (75 Mhz, CDCl$_3$): δ=9.0, 22.4, 25.8, 27.8, 29.1, 29.1, 29.1, 29.3, 29.3, 32.9, 50.3, 54.2, 66.9, 168.5 C$_{16}$H$_{33}$NO$_4$Si calc. C 57.97 H 10.03 N 4.22 (331.53) obs. 58.14 9.82 4.22 MS (EL): m/z=331 (M$^+$, 12), 85 (100), 98 (92) HRMS: m/z calc. for C$_{16}$H$_{33}$NO$_4$Si 331.2179, obs. 331.2186.

1.3 Example 3

Production of 2-[3-(triethoxysilyl)propyl]-1,3-oxazoline

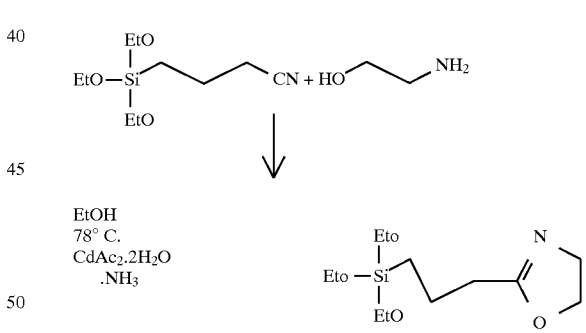

A mixture of
  50 ml ethanol abs. water-free,
  2.5 ml (11.2 mmoles) 3-cyanopropyltriethoxysilane,
  0.67 ml (11.2 mmoles) 2-aminoethanol, and
  0.12 g (0.22 mmoles) cadmium acetate dihydrate was heated for 20 h until reflux in a round-bottomed flask with reflux condenser and inlet tube for protective gas.

The 2-[3-(triethoxysilyl)propyl]-1,3-oxazoline was produced in 25% conversion. IR (KBr): ν=2920, 1668, 1110, 950 cm$^{-1}$ $^1$H-NMR: 4.15, 3.80 ppm (oxazoline)

2. Modification of surfaces

2.1 Example 1

A suspension of
  700 ml methanol, 70 ml water (deionized), 15 ml ammonium hydroxide solution (25% by weight-in water), 10 g Aerosil® 200, pyrogenically produced $SiO_2$, spec. surface 200 $m^2/g$ 3.85 g (10.3 mmoles) 2-[10-triethoxysilyl)decyl]-1,3-oxazoline was heated for 2 h to an internal temperature of 50° C. in a round-bottomed flask with internal thermometer and reflux condenser. The filtered-off $SiO_2$ was subsequently dried 4 h at 30° C./oil pump vacuum, then 2 h at 80° C./oil pump vacuum.

IR (KBr): $\nu$=2927, 2855, 1641 (C=N) $cm^{-1}$ Thermogravimetry (25°–700° C.): 10.1% by weight (48 mmoles decyloxazoline/100 g Aerosil 200) Elementary analysis: 44 mmoles/100 g Aerosil 200 $^{29}$Si-CP-MAS-NMR: −60 ppm $T_2$−64 ppm $T_3+T_4$.

2.2 Example 2

A suspension of 300 ml toluene abs. water-free, 10.0 g Aerosil® 200, pyrogenically produced $SiO_2$, 11.2 g (30 mmoles) 2-[10-triethoxysilyl)decyl]-1,3-oxazoline was heated for 2 h to an internal temperature of 50° C. in an agitated flask with internal thermometer and reflux cooler. The filtered-off $SiO_2$ was subsequently dried 4 h at 30° C./oil pump vacuum, then 2 h at 80° C./oil pump vacuum.

IR (KBr): $\nu$=2927, 2855, 1641 (C=N) $cm^{-1}$ Thermogravimetry (25°–700° C.):4.6% by weight (22 mmoles decyloxazoline/100 g Aerosil 200) Elementary analysis: 21 mmoles/100 g Aerosil 200 $^{29}$Si-CP-MAS-NMR: 55 ppm (standard TMS) $T_1$−59 ppm $T_2$.

2.3 Example 3

The work was carried out analogously to the method in example 2 with an amine catalyst wherein 300 ml toluene abs. water-free, 10.0 g Aerosil 200, 11.2 g (30 mmoles) 2-[10-(triethoxysilyl)decyl]-1,3-oxazoline, and 1.1 ml (10 mmoles) benzylamine was heated for 48 h until reflux. The filtered-off $SiO_2$ was subsequently extracted 24 h with toluene, then dried in an oil pump vacuum at 60° C. for 5 h.

IR (KBR): $\nu$=2926, 2855, 1640 (C=N) $cm^{-1}$ Thermogravimetry (25°–700° C.): 6.5% by weight (31 mmoles decyloxazoline/100 g Aerosil 200) Elementary analysis: 30 mmoles/100 g Aerosil 200 $^{29}$Si-CP-MASNMR: −59.5 ppm $T_2$−63.5 $T_3+T_4$.

2.4 Example 4

A suspension of 700 ml methanol, 70 ml water (deionized), 15 ml ammonium hydroxide solution (25% by weight in water), 100 glass spheres CP 5000-00, 3.85 g (10.3 mmoles) 2-[10-(triethoxysilyl)decyl]-1,3-oxazoline was heated for 2 h to an internal temperature of 50° C. in a round-bottomed flask with internal thermometer and reflux condenser. The filtered-off $SiO_2$ was subsequently dried 4 h at 30° C./oil pump vacuum, then 2 h at 80° C./oil pump vacuum.

Thermogravimetry (25°–650° C.): 0.20% by weight (0.95 mmole decyloxazoline/100 g glass bulbs). Manufacturer of the glass spheres: Potters Ballotini, Kirchheim-Bollanden Type: CP 5000-00 untreated, non-silanized average dimension 5–10 $\mu$m, 99%<12 $\mu$m

3. The use of the modified materials

Two series with three types of glass spheres were tested. In the Series I experiments, the amount of filler was varied at a constant adhesion promoter content (10% by volume). In the Series II experiments, the amount of adhesion promoter was varied at a constant filler content (10% by volume). The adhesion promoter used in the following examples is carboxylated polypropylene and the fillers are glass spheres as further described below.

The composites were produced in a Haake Rheomix 90 kneader with a 60 ml Zweihaken mixing chamber at 60 rpm and 240° C. with a total reaction time of six minutes. The components were mixed in varying percentage by volume amounts. After the reaction the material obtained was melt-pressed to plates 2 mm thick from which specimens were milled according to DIN for stress-strain measurements.

The maximum tensile stress theoretically possible of the non-filled matrix is achieved in the composite obtained by the covalent bonding of the carboxylated PP on oxazoline-functionalized micro-glass spheres. By way of comparison the glass spheres coated with octylsilane, which differ structurally only by the lack of oxazoline, and the untreated glass spheres have considerably reduced tensile stresses (table and graph 1).

Matrix polypropylene: PPn; Shell KM 6100 Adhesion promoter PP-COOH, Polybond BP Chemicals, acrylic acid (6% by weight) grafted PP, $M_W$=30000–40000 Filler glass spheres: Potters Ballotini CP 50000-00, $d_{99}$=12 $\mu$m a) Untreated b) Silanized with oxazolinyldecyltriethoxysilane, 0.95 mmole/100 g c) Silanized with octyltriethoxysilane, 1.0 mmole/100 g

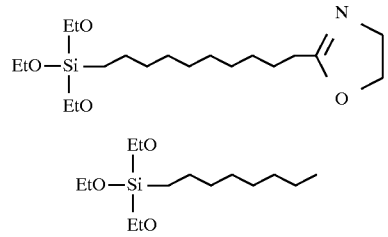

3.2 Series I: PPn+10% by volume PP-COOH+x % by volume (0, 10, 20, 30) glass a), b), c)

TABLE 1

| Type | Glass % by vol. | E-modulus (Mpa) | Tensile stress (Mpa) | Elongation at tear |
|---|---|---|---|---|
| — | 0 | 1230 | 30.0 | 20 |
| a) | 10 | 1490 | 29.0 | 10 |
| b) | 10 | 1510 | 34.0 | 9 |
| c) | 10 | 1510 | 28.1 | 38 |
| a) | 20 | 1770 | 27.0 | 4 |
| b) | 20 | 1940 | 34.0 | 8 |
| c) | 20 | 1890 | 22.2 | 44 |
| a) | 30 | 2490 | 25.8 | 4 |
| b) | 30 | 2440 | 33.6 | 4 |
| c) | 30 | 2261 | 18.4 | 24 |

See FIG. 1 for a graph of these results.

3.3 Series II: PPn+x % by volume (0, 1, 2, 5, 10) PP-COOH+10% by volume glass a), b)

TABLE 2

| Type | PP-COOH % by vol. | E-modulus (Mpa) | Tensile stress (Mpa) | Elongation at tear |
|------|-------------------|-----------------|----------------------|--------------------|
| a)   | 0                 | 1340            | 26.7                 | 380                |
| b)   | 0                 | 1380            | 28.2                 | 60                 |
| a)   | 1                 | 1430            | 27.0                 | 40                 |
| b)   | 1                 | 1430            | 29.7                 | 33                 |
| a)   | 2                 | 1440            | 27.7                 | 18                 |
| b)   | 2                 | 1530            | 30.5                 | 12                 |
| a)   | 5                 | 1540            | 28.0                 | 13                 |
| b)   | 5                 | 1490            | 32.5                 | 15                 |
| a)   | 10                | 1490            | 29.0                 | 10                 |
| b)   | 10                | 1510            | 34.0                 | 9                  |

Figure 2:
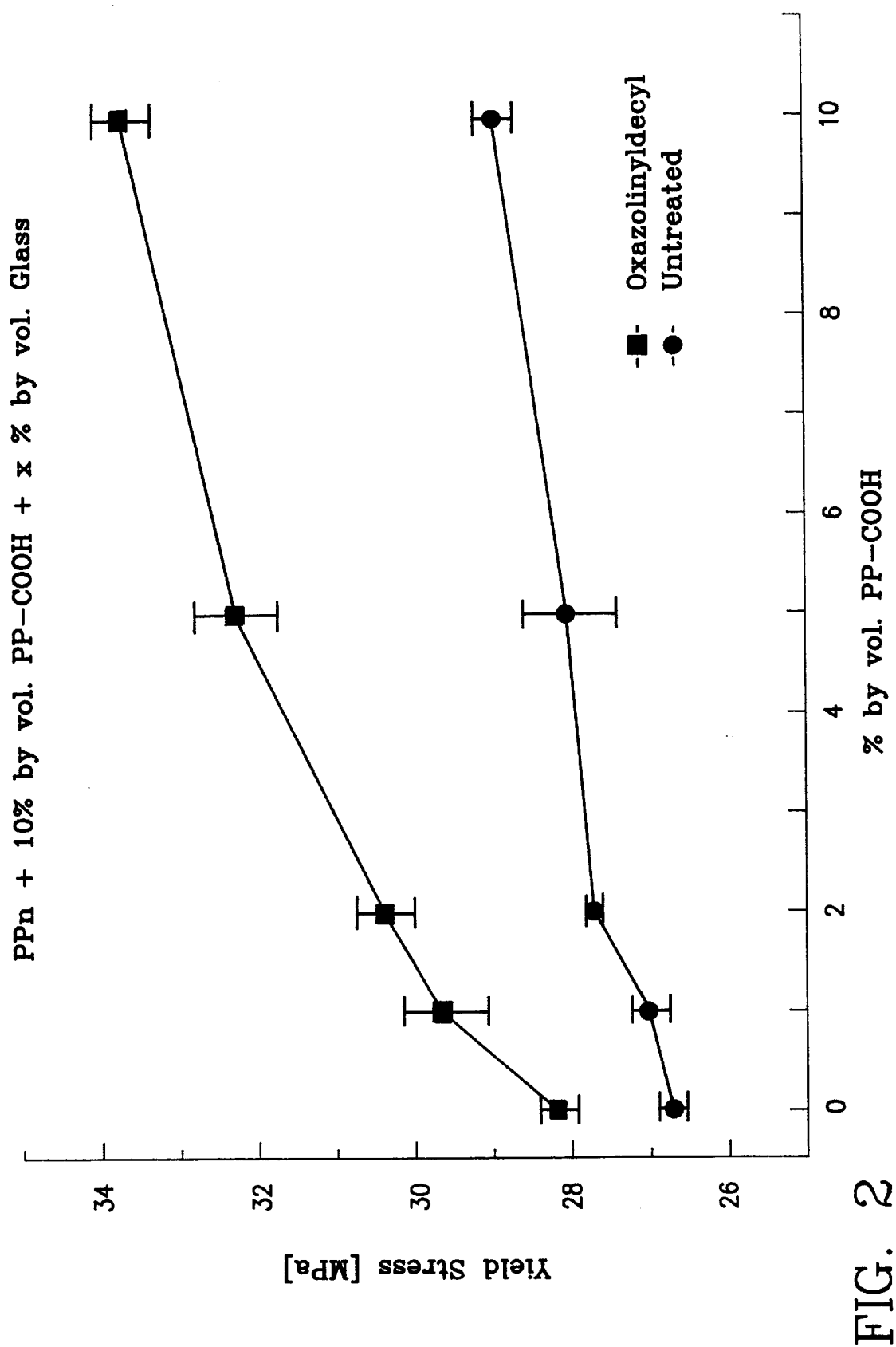
FIG. 2: The results of the Series II experiments as listed in Table 2 are graphed comparing the tensile stress of polypropylene, which contains oxazoline-functionalized glass spheres covalently bonded to carboxylated polypropylene according to the invention, with polypropylene that contains untreated glass spheres. The volume of the adhesion promoter (carboxylated polypropylene) in the Series II experiments was varied, and the results were graphed at 0%, 1%, 2%, 5%, and 10% by volume. The volume of the glass spheres filler was held constant at 10% by volume.

See FIG. 2 for a graph of these results

Further variations and modifications of the foregoing will be apparent to those skilled in the art and are intended to be encompassed by the claims, appended hereto.

German priority application 196 06 413.9 is relied on and incorporated herein by reference.

We claim:

1. A compound which is an alkylalkoxysilyl-1,3-oxazoline of the formula

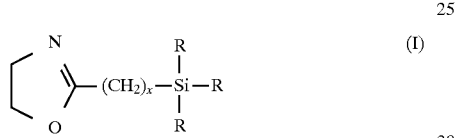

(I)

wherein R is a member selected from the group consisting of alkyl with 1 to 6 C atoms, branched or unbranched, alkoxy with 1 to 4 C atoms, and phenyl wherein Si is bonded to at least one alkoxy group; and wherein x signifies a whole number of 2 to 14.

2. The compound as defined in claim 1 wherein the said alkylalkoxysilyl-1,3-oxazoline is 2-[10-(triethoxysilyl)decyl]-1,3-oxazoline.

3. The compound as defined in claim 1 wherein the said alkylalkoxysilyl-1,3-oxazoline is 2-[10-(trimethoxysilyl)decyl]-1,3-oxazoline.

4. The compound as defined in claim 1 wherein the said alkylalkoxysilyl-1,3-oxazoline is 2-[3-triethoxysilyl)propyl]-1,3-oxazoline.

5. A method of producing the alkylalkoxysilyl-1,3-oxazoline as defined in claim 1 comprising reacting 2-(alkenyl)-1,3-oxazoline of the formula

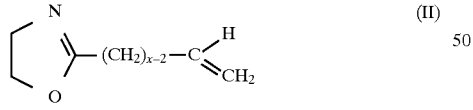

(II)

wherein x is a whole number of 2 to 14, with an alkylalkoxysilane of the formula

(III)

wherein R is a member selected from the group consisting of branched or unbranched alkyl having 1–6 carbon atoms, alkoxy having 1–4 carbon atoms, or phenyl;

wherein said 2-(alkenyl)-1,3-oxazoline and alkylalkoxysilane are reacted in the presence of a Pt or rhodium catalyst.

6. The method as defined in claim 5, wherein said reaction takes place at a temperature of 80° to 140° C.

7. The method as defined in claim 5, wherein pressure is adjusted by the vapor pressure of the reactants;

wherein said reaction takes place under protective gas; and wherein a solvent is present which comprises an additional amount of said 2-(alkenyl)-1,3-oxazoline or an inert, organic solvent which dissolves said 2-(alkenyl)-1,3-oxazoline and said alkylalkoxysilane.

8. The method as defined in claim 5 wherein the amount of said 2-(alkenyl)-1,3-oxazoline and said alkylalkoxysilane is in a molar ratio of 1:1 to 2.0:1.

9. The method as defined in claim 8 wherein the amount of said molar ratio is 1.2:1 to 1.7:1.

10. The method as defined in claim 5 wherein 2-(9-decenyl)-1,3-oxazoline is reacted with triethoxysilane to form 2-[10-(triethoxysilyl)decyl]-1,3-oxazoline.

11. The method as defined in claim 5 wherein 2-(9-decenyl)-1,3-oxazoline is reacted with trimethoxysilane to form 2-[10-(trimethoxysilyl)decyl]-1,3-oxazoline.

12. A method of producing the alkylalkoxysilyl-1,3-oxazoline as defined in claim 1 comprising reacting an amino alcohol with cyanosilane compound of the formula $$NC-(CH_2)_y-\underset{\underset{R}{|}}{\overset{\overset{R}{|}}{Si}}-R \qquad (IV)$$

wherein R is a member selected from the group consisting of branched or unbranched alkyl having 1–6 carbon atoms, alkoxy having 1–4 carbon atoms, or phenyl;

wherein said 2-(alkenyl)-1,3-oxazoline and alkylalkoxy silane is reacted in the presence of a Pt or rhodium catalyst, y is a whole number from 2 to 12; and said amino alcohol and said cyanosilane compound is reacted in the presence of a Cd salt acting as catalyst.

13. The method as defined in claim 12 wherein said amino alcohol is 2-aminoethanol.

14. The method as defined in claim 13, wherein 2-aminoethanol is reacted with 3-cyanopropyltriethoxysilane to form 2-[3-(triethoxysilyl)propyl]-1,3-oxazoline.

15. The method as defined in claim 12, wherein said reaction takes place at a temperature of 60° to 140° C.

16. The method as defined in claim 14, wherein pressure is adjusted by the vapor pressure of the reactants.

17. The method as defined in claim 13 wherein the amount of said cyanosilane and said 2-aminoethanol is present in a molar ratio of 1.2:1 to 1:1.2.

18. The method as defined in claim 12 wherein a catalyst is present comprising soluble cadmium salts in a molar amount of 0.1 to 3% relative to the amount of cyanosilane compound.

* * * * *